United States Patent [19]
Green et al.

[11] Patent Number: 6,051,742
[45] Date of Patent: Apr. 18, 2000

[54] PROCESS FOR PREPARING CHLOROHYDRINS

[75] Inventors: Daniel P. Green; John Klier, both of Midland; Christopher J. Tucker, Bay City; Michael S. Ferritto, Midland, all of Mich.

[73] Assignee: The Dow Chemical Company, Midland, Mich.

[21] Appl. No.: 09/211,284

[22] Filed: Dec. 14, 1998

[51] Int. Cl.7 .................................................... C07C 31/36
[52] U.S. Cl. .................................................................. 568/850
[58] Field of Search ............................................. 568/850

[56] References Cited

U.S. PATENT DOCUMENTS

| | | | |
|---|---|---|---|
| 3,277,187 | 10/1966 | Dewhirst | 568/850 |
| 3,598,884 | 8/1971 | Kloss et al. | 568/850 |
| 3,845,145 | 10/1974 | Wojtowicz et al. | 568/850 |
| 4,496,777 | 1/1985 | Suciu et al. | 568/850 |
| 4,696,726 | 9/1987 | Blytas et al. | 568/850 |
| 5,523,425 | 6/1996 | Pech et al. | 568/850 |

*Primary Examiner*—Amelia Owens

[57] ABSTRACT

A process for hypochlorinating unsaturated alpha-olefins to produce chlorohydrins which comprises forming a microemulsion of water and an unsaturated alpha-olefin and then adding an oxidant to the microemulsion under conditions sufficient to form the chlorohydrins. The microemulsion is formed by adding a non-nucleophilic surfactant and, optionally, a co-surfactant, to the mixture of water and unsaturated alpha-olefin.

29 Claims, No Drawings

PROCESS FOR PREPARING CHLOROHYDRINS

BACKGROUND OF THE INVENTION

This invention relates to the preparation of chlorohydrins. More particularly, this invention relates to the preparation of chlorohydrins by hypochlorination of alpha-olefins. The chlorohydrins are useful as intermediates in the preparation of epoxides.

Conventional hypochlorination technology involves the reaction of chlorine with an alpha-olefin in water to yield the corresponding chlorohydrin. This reaction results in the formation of an excess oil phase due to the incompatibility of olefin with water or due to the formation of water-insoluble by-products. This oil phase is thought to serve as a locus for the production of undesired by-products such as dichlorides and ethers. To compensate for the incompatibility of olefin or by-products with water and reduce the formation of excess oil, large amounts of water relative to the olefin and intense mechanical mixing are used. This practice, however, causes in the subsequent dehydrochlorination of the chlorohydrin, the formation of significant volume of aqueous effluents containing organic impurities, the purification of which requires expensive treatments.

U.S. Pat. No. 5,146,011 describes a process for preparing chlorohydrins by reacting a concentrated, aqueous solution of hypochlorous acid with an unsaturated organic compound having from 2 to about 10 carbon atoms and selected from the group consisting of substituted and unsubstituted olefins and cyclic olefins. The process is optionally carried out in the presence of a surfactant such as nonylphenol ethoxylate, alkyldimethylbenzylammonium chloride and sodium dodecylbenzenesulfate, all of which contain an aromatic ring. It is known that any surfactant which contains an aromatic ring is subject to rapid oxidative reaction with chlorine or HOCl in the reaction mixture. The reaction is at temperatures from the freezing point of water up to 55° C. The low reaction temperature requires use of heat exchange equipment to remove the heat of reaction. The process requires the use of high concentration (greater than 10 weight percent, preferably from 20 to 65, most preferably from 35 to 55 percent by weight) HOCl solutions.

British Patent Application 2 029 821 A describes a process for preparing glycerol dichlorohydrins by reacting chlorine and an emulsion of allyl chloride in water. The process requires the preparation of an emulsion of allyl chloride in water using a static mixer prior to feeding the emulsion to the reactor. To facilitate the formation of the allyl chloride-water emulsion, an emulsifier, such as a non-ionic or anionic emulsifier, is added to the allyl chloride-water mixture. In this process the reaction between the allyl chloride-water emulsion and chlorine takes place in the oily phase which produces undesirable by-products.

It would be desirable to provide a process for preparing chlorohydrins which do not have the disadvantages of the known processes described above.

SUMMARY OF THE INVENTION

In a first aspect, this invention is a process for hypochlorinating unsaturated alpha-olefins to produce chlorohydrins which comprises forming a microemulsion of water and an unsaturated alpha-olefin and then adding an oxidant to the microemulsion under conditions sufficient to form the chlorohydrin.

DETAILED DESCRIPTION OF THE INVENTION

In general, the process for hypochlorinating unsaturated alpha-olefins to produce chlorohydrins comprises forming a microemulsion of water and an unsaturated alpha-olefin and then adding an oxidant to the microemulsion under conditions sufficient to form the chlorohydrins. The resulting microemulsion also comprises water-insoluble reaction by-products.

Microemulsions are optically isotropic, transparent or translucent, and thermodynamically stable dispersions of two immiscible liquids stabilized by a combination of non-ionic amphipatic surface active materials and long-chain alcohols or amines. Their properties are time independent. They are independent of the order of mixing, and they return to their original state when subjected to a small disturbance which is subsequently relaxed. On the other hand, emulsions are thermodynamically unstable. The drops of dispersed phase are generally large, perhaps larger than 0.1 $\mu$m, so that emulsions often take on a milky rather than the transparent or translucent appearance generally associated with microemulsions. The average drop size of emulsions grows continuously with time, which is a manifestation of thermodynamic instability. When exposed to a body force proportional to the mass, such as a gravitational field, emulsions will ultimately separate into two distinct phases.

The formation of an emulsion involves an increase in the interfacial area between two immiscible phases and is accompanied by an increase in free energy. For the formation of a microemulsion, the interfacial tension has to be lowered to very low values, which is done by adsorption at the interface of a surface active material. For emulsions, no such interfacial tension lowering is needed to form the emulsions. Although not intended to be bound by theory, it is believed that when the interfacial tension is lowered to near zero, the system emulsifies spontaneously, creating a microemulsion. Microemulsions are described in "Microemulsions And Related Systems", 1988, Bourell & Schecter, Marcel Dekker Inc, New York and U.S. Pat. No. 5,597,792.

In general, the microemulsion is prepared by mixing water and an unsaturated alpha-olefin and then adding to the mixture a surfactant which is capable of forming a microemulsion of the olefin in water in the presence of the reaction products. The microemulsion of water and unsaturated alpha-olefin is spontaneously formed upon the addition of the surfactant to the water and olefin mixture. Preferably, the surfactant is combined with a co-surfactant. Preferably, the reaction product (e.g. a chlorohydrin) is used as the co-surfactant. Optionally, additional co-surfactants may be added to enhance formation of the microemulsion. The surfactant may be dissolved (premixed) in either the starting olefinic substrate or the water, depending on the solubility characteristics of the specific surfactant utilized. While emulsified particles typically do not have dynamic interface and exchange with other particles, microemulsified oil has very rapidly exchanging oil phase(s) and dynamic interface which greatly facilitate phase transfer and interfacial kinetics, both of which are desirable and necessary for improved chlorohydrin selectivity.

The unsaturated alpha-olefins which can be employed in the practice of the present invention for preparing the chlorohydrins include unsaturated organic compounds containing from 2 to about 24 carbon atoms and selected from the group consisting of substituted and unsubstituted olefins, diolefins and cyclic olefins, wherein the substituent(s) is alkyl, phenyl, or alkylphenyl. Examples of these olefins are 1-pentene, 1-octene, 1dodecene, 1-tetradecene, 1-hexadecene, 1-eicosene, 2-hexene, 4-decene, 5-dodecene, 7-tetradecene,and 9-eicosene. Mixtures of these olefins can also be hypochlorinated to form chlorohydrins. The bis allyl ethers can also be employed in the practice of the present invention.

The surfactants which can be employed in the practice of the present invention for preparing the chlorohydrins are preferably non-nucleophilic. The term "non-nucleophilic" as used herein, refers to surfactants which do not readily react with chloronium ion, the key reactive intermediate formed by reaction of chlorine with olefin. Additionally, the surfactant should not readily react with chlorine.

The non-nucleophilic surfactants which can be employed in the practice of the present invention for preparing the chlorohydrins include alpha-olefin in sulfonates, such as those prepared from 1-octene up through $C_{20}$ to $C_{24}$ alpha-olefin (see I Yamane, O. Okumura; "Surfactants: AOS" in Alpha Olefins Applications Handbook, G. R. Lapin and J. D. Sauer Ed.; Marcel Dekker, New York, NY, 1989, pp. 201–239); quaternary amines, and alpha-olefin in carboxylates.

The quaternary amines which can be employed in the practice of the present invention include dodecyltrimethyl ammonium chloride, octadecyl trimethyl ammonium chloride, octadecyl pyridium chloride, didodecyldimethyl ammonium chloride, tallow ammonium chloride and 1-benzyl-2-hexadecyl ammonium chloride.

Other surfactants which can be employed in the practice of the present invention include alkyl sulfonates, alkyl sulfates, dialkyl sulfosuccinates, fatty acid salts, and alkyl trimethyl ammonium chlorides. The co-surfactants which can be employed in the practice of the present invention include non-nucleophilic alcohols and carboxylates, and hydrophilic organic acids such as acetic acid, propionic acid, and butyric acid. The preferred co-surfactants are t-butanol, 1,1-dimethyl-1-propanol and 1,1dimethyl-1-butanol, the most preferred being the chlorohydrins themselves which are formed during the reaction.

The oxidants which can be employed in the practice of the present invention for preparing the chlorohydrin include chlorine, hypochlorous acid (HOCL) and tert-butylhypochlorite (t-BuOCL).

The conditions at which the hypochlorination reaction is most advantageously conducted are dependent on a variety of factors, including the specific reactants and catalyst employed, if any. In general, the reaction is conducted at room temperature up to 100° C. Either plug flow reactor conditions or continuous stirred tank reactor (CSTR) conditions can be employed. With the latter reactor design, one can optionally add both caustic and chlorine to the reaction vessel in order to maintain a given pH, usually between pH=1 and pH=7, a process which is sometimes referred to as a half bleach process.

The time and temperature most advantageously employed will vary depending on the specific reactants employed, particularly their reactivity. In general, the reaction temperature to form the chlorohydrins is from 0° C. to 120° C. and, most preferably, from 20° C. to 80° C., and for a time sufficient for the reaction to occur, which may be as short as 10 seconds in a continuous or plug flow reactor. Preferably, such time period is from 1 minute to 2 hours, more preferably from 5 minutes to ½ hour and, most preferably, from 10 minutes to ¼ hour. The time indicated is residence time in a continuous reactor regime.

The concentrations at which the reactants are most advantageously employed are dependent on a variety of factors including the specific alpha-olefins employed and the chlorohydrins being prepared.

In general, the water to alpha-olefins volume ratio is at least 5 to 1 and preferably at least 20 to 1. In most cases, the water to alpha-olefins volume ratio does not exceed 100 to 1.

In general, the oxidants can be employed in an amount of from about 0.8 to about 1.2 equivalents based on olefin, preferably, from about 0.9 to about 1.1, more preferably from about 0.95 to about 1.05 and, most preferably 1.0 equivalent, based on olefin. Normally the oxidant:olefin ratio is 1:1 at standard reaction conditions for hypochlorination processes.

The amount of surfactants which can be employed is, in general, from about 0.01 to about 5 weight percent, preferably, from about 0.1 to about 2 weight percent, more preferably from about 0.2 to about 1.5 weight percent and, most preferably from about 0.3 to 1.0 weight percent, based on the weight of the olefin.

The following working examples are given to illustrate the invention and should not be construed as limiting its scope. Unless otherwise indicated, all parts and percentages are by weight.

EXAMPLE 1

Hypochlorination of 1-octene with t-BuOCL in Water

Into a 500 mL jacketed resin kettle was added 200 mL of water, 0.625 g of $C_{20-24}$ alpha-olefin sulfonate (sodium salt, 40% in water) and 0.4 g of sodium sulfate. The reaction vessel was fitted with constant speed, variable torque mechanical stirrer, pH meter, thermometer, dry ice condenser vented to a bubbler, and septum. The mixture was stirred at 500 rpm and heated to 40° C. and t-BuOCL (98%, 5.32 g, 0.0491 mole) and 1-octene (5 g, 7.37 mL, 0.045 mole) were added at equimolar rates using syringe pumps over a 1 hour period. After the addition was complete, NaOH was added (0.05 mole) until the pH reached 9.4 to convert the chlorohydrins formed to the corresponding epoxides. The solution was analyzed by GC which showed 92% 1,2-epoxyoctane, 1.4% 1,2-dichlorooctane and 6.5% bisether by-products.

EXAMPLE 2

Hypochlorination of 1-hexene with t-BuOCL in Water

Into a 500 mL jacketed resin kettle was added 200 mL of water, 0.625 g of $C_{20-24}$ alpha-olefin sulfonate (sodium salt, 40% in water) and 0.4 g of sodium sulfate. The reaction vessel was fitted with constant speed, variable torque mechanical stirrer, pH meter, thermometer, dry ice condenser vented to a bubbler, and septum. NaOH was added until the pH reached 10. The mixture was stirred at 500 rpm and heated to 40° C. and t-BuOCL (98%, 7.74 g, 0.0713 mole) and 1-hexene (5 g, 7.4 mL, 0.0594 mole) were added at equimolar rates using syringe pumps over a 1 hour period. After the addition was complete, NaOH was added (0.05 mole) until the pH reached 10 to convert the chlorohydrins formed to the corresponding epoxides. The solution was analyzed by GC which showed 95% 1,2-epoxyhexane, 2.7% 1,2-dichlorohexane and 3.2% bisether by-products.

EXAMPLE 3

Into a 500 mL jacketed resin kettle equipped with a mechanical stirrer, pH probe, chlorine gas bubbler, and addition pumps for adding olefin and aqueous sodium hydroxide was placed 400 mL of water and 0.09 g of Sodium $C_{14-16}$ alpha-olefin sulfonate. The mechanical stirrer was set at 2000 rpm. To this was added over 5 minutes, 8 g of hexene (0.095 moles), 6.75 g of Chlorine gas and sufficient aqueous NaOH to maintain the pH at 6.5 to 7.0. After this time 20 mL of 5N NaOH was added to the reactor to convert the chlorohydrins formed to the corresponding epoxides. The reactor contents were analyzed via Gas Chromatography and gave the following results:

75.2% Epoxy Hexane 13.1% Dichlorohexane 11.7% Bis-(chlorohexyl ether)

EXAMPLE 4

The procedure of Example 3 was repeated except 0.045 g of sodium $C_{14-16}$ alpha-olefin sulfonate was added instead of 0.09 g. The reactor contents were analyzed via Gas Chromatography and gave the following results:

70.2% Epoxy Hexane 17.0% Dichlorohexane 12.8% Bis-(chlorohexyl ether)

EXAMPLE 5

The procedure of Example 3 was repeated except 0.0225 g of sodium $C_{14-16}$ alpha-olefin sulfonate was added instead of 0.09 g. The reactor contents were analyzed via Gas Chromatography and gave the following results:

48.6% Epoxy Hexane 30.6% Dichlorohexane 20.8% Bis-(chlorohexyl ether)

EXAMPLE 6

The procedure of Example 3 was repeated except 0.225 g of sodium dodecyl sulfate instead of sodium $C_{14-16}$ alpha-olefin sulfonate was added. The reactor contents were analyzed via Gas Chromatography and gave the following results:

84.5% Epoxy Hexane 6.2% Dichlorohexane 9.3% Bis-(chlorohexyl ether)

EXAMPLE 7

The procedure of Example 3 was repeated except 0.1125 g of sodium dodecyl sulfate instead of sodium $C_{(14-16)}$ alpha-olefin sulfonate was added. The reactor contents were analyzed via gas chromatography and gave the following results:

77.4% Epoxy Hexane 11.1% Dichlorohexane 11.5% Bis-(chlorohexyl ether)

EXAMPLE 8

The procedure of Example 3 was repeated except 0.056 g of sodium dodecyl sulfate instead of sodium $C_{14-16}$ alpha-olefin sulfonate was added. The reactor contents were analyzed via gas chromatography and gave the following results:

60.9% Epoxy Hexane 22.1% Dichlorohexane 17.0% Bis-(chlorohexyl ether)

EXAMPLE 9

The procedure of Example 3 was repeated except 0.90 g of Steol CS-130 (0.220 g active sulfates of ethoxylated alcohols) instead of sodium $C_{14-16}$ alpha-olefin sulfonate was added. The reactor contents were analyzed via gas chromatography and gave the following results:

78.0% Epoxy Hexane 10.8% Dichlorohexane 11.2% Bis-(chlorohexyl ether)

EXAMPLE 10

The procedure of Example 3 was repeated except 0.45 g of Steol CS-130 (0.110 g active sulfates of ethoxylated alcohols) instead of sodium $C_{14-16}$ alpha-olefin sulfonate was added. The reactor contents were analyzed via gas chromatography and gave the following results:

79.9% Epoxy Hexane 11.5% Dichlorohexane 8.6% Bis-(chlorohexyl ether)

EXAMPLE 11

The procedure of Example 3 was repeated except 0.225 g of Steol CS-130 (0.055 g active sulfates of ethoxylated alcohols) instead of sodium $C_{14-16}$ alpha-olefin sulfonate was added. The reactor contents were analyzed via Gas Chromatography and gave the following results:

67.8% Epoxy Hexane 16.9% Dichlorohexane 15.3% Bis-(chlorohexyl ether)

COMPARATIVE EXAMPLE A

The procedure of Example 3 was repeated except 0.225 g of sodium octyl sulfonate instead of sodium $C_{14-16}$ alpha-olefin sulfonate was added. The reactor contents were analyzed via gas chromatography and gave the following results:

38.9% Epoxy Hexane 41.9 % Dichlorohexane 19.2 % Bis-(chlorohexyl ether)

No microemulsification of product was observed. Instead, macroemulsions formed.

EXAMPLE 12

The procedure of Example 3 was repeated except 0.225 g of sodium decyl sulfonate instead of sodium $C_{14-16}$ alpha-olefin sulfonate was added. The reactor contents were analyzed via gas chromatography and gave the following results:

68.7 % Epoxy Hexane 19.8 % Dichlorohexane 11.5 % Bis-(chlorohexyl ether)

EXAMPLE 13

The procedure of Example 3 was repeated except 0.225 g of sodium dodecyl sulfonate instead of sodium $C_{14-16}$ alpha-olefin sulfonate was added. The reactor contents were analyzed via gas chromatography and gave the following results.

81.1 % Epoxy Hexane 8.2 % Dichlorohexane 10.7 % Bis-(chlorohexyl ether)

COMPARATIVE EXAMPLE B

The procedure of Example 3 was repeated except 0.225 g of sodium hexadecyl sulfonate instead of sodium $C_{14-16}$ alpha-olefin sulfonate was added. The reactor contents were analyzed via gas chromatography and gave the following results:

45.8% Epoxy Hexane 31.8% Dichlorohexane 22.4% Bis-(chlorohexyl ether)

No microemulsification of product was observed. Instead, macroemulsions formed.

COMPARATIVE EXAMPLE C

The procedure of Example 3 was repeated except no surfactant was added. The reactor contents were analyzed via gas chromatography and gave the following results.

30.1% Epoxy Hexane 52.3% Dichlorohexane 17.6% Bis-(chlorohexyl ether)

EXAMPLE 14

Into a 500 mL jacketed resin kettle equipped with a mechanical stirrer, pH probe, chlorine gas bubbler, and an addition pump for adding olefin was placed 400 mL of water and 0.20 g of sodium $C_{14-16}$ alpha-olefin sulfonate. The mechanical stirrer was set at 2000 rpm. To this was added over 40 minutes, 20 g of allyl chloride (0.264 moles) and 18.56 g of Chlorine gas. The reactor contents were analyzed via gas chromatography and gave the following results.

95.56% Allyl chloride Chlorohydrin 3.76% Trichloropropane 0.68% dichloropropyl ethers

EXAMPLE 15

Into a 500 mL jacketed resin kettle equipped with a mechanical stirrer, pH probe, chlorine gas bubbler, and an addition pump for adding olefin was placed 400 mL of water and 0.20 g of sodium $C_{14-16}$ alpha-olefin sulfonate. The mechanical stirrer was set at 750 rpm. To this was added over 40 minutes, 20 g of allyl chloride (0.264 moles) and 18.56 g of chlorine gas. The reactor contents were analyzed via gas chromatography and gave the following results:

93.52% Allyl chloride Chlorohydrin 5.36% Trichloropropane 1.16% dichloropropyl ethers

EXAMPLE 16

Into a 500 mL jacketed resin kettle equipped with a mechanical stirrer, pH probe, chlorine gas bubbler, and an addition pump for adding olefin was placed 400 mL of water and 0.10 g of sodium $C_{14-16}$ alpha-olefin sulfonate. The mechanical stirrer was set at 750 rpm. To this was added over 40 minutes, 20 g of allyl chloride (0.264 moles) and 18.56 g of chlorine gas. The reactor contents were analyzed via gas chromatography and gave the following results.

93.65% Allyl chloride Chlorohydrin 5.23% Trichloropropane 1.12% dichloropropyl ethers

EXAMPLE 17

Into a 500 mL jacketed resin kettle equipped with a mechanical stirrer, pH probe, chlorine gas bubbler, and an addition pump for adding olefin was placed 400 mL of water and 0.02 g of sodium $C_{14-16}$ alpha-olefin sulfonate. The mechanical stirrer was set at 750 rpm. To this was added over 40 minutes, 20 g of allyl chloride (0.264 moles) and 18.56 g of Chlorine gas. The reactor contents were analyzed via gas chromatography and gave the following results:

85.82% Allyl chloride Chlorohydrin 10.27% Trichloropropane 3.91% dichloropropyl ethers

COMPARATIVE EXAMPLE D

Into a 500 mL jacketed resin kettle equipped with a mechanical stirrer, pH probe, chlorine gas bubbler, and an addition pump for adding olefin was placed 400 mL of water. The mechanical stirrer was set at 750 rpm. To this was added over 40 minutes, 20 g of allyl chloride (0.264 moles) and 18.56 g of chlorine gas. The reactor contents were analyzed via gas chromatography and gave the following results.

61.22% Allyl chloride Chlorohydrin 33.85% Trichloropropane 4.93% dichloropropyl ethers

COMPARATIVE EXAMPLE E

Into a 500 mL jacketed resin kettle equipped with a mechanical stirrer, pH probe, chlorine gas bubbler, and an addition pump for adding olefin was placed 400 mL of water. The mechanical stirrer was set at 2000 rpm. To this was added over 40 minutes, 20 g of allyl chloride (0.264 moles) and 18.56 g of Chlorine gas. The reactor contents were analyzed via Gas Chromatography and gave the following results.

74.13% Allyl chloride Chlorohydrin 17.80% Trichloropropane 8.07% dichloropropyl ethers In the above examples, Examples 3–5, 6–8 and 9–11 demonstrate the dependence of chlorohydrin yield on the amount of surfactant for the preparation of epoxy hexene using three surfactants which exhibited three phase microemulsion behavior. Examples 12 and 13 and Comparative Examples A and B show the effect of alkyl tail length on chlorohydrin yield. The surfactants used in Comparative Examples A and B gave emulsions and resulted in only slight improvements in chlorohydrin yield while the surfactants used in Examples 12 and 13 gave microemulsions and resulted in substantially better overall chlorohydrin yields. In Comparative Example C, no surfactant was used, and a poor yield was obtained. Examples 14–17 and Comparative Examples D and E describe the hypochlorination of allyl chloride with chlorine. Examples 14–17 show the effect of added surfactant as well as agitation rate on chorohydrin yield. Comparative Examples D and E show the yields obtained when no surfactant is added at the two agitation rates used.

What is claimed is:

1. A process for hypochlorinating unsaturated alpha-olefins to produce chlorohydrins which comprises forming a microemulsion of water and an unsaturated alpha-olefin and then adding an oxidant to the microemulsion under conditions sufficient to form the chlorohydrins.

2. The process of claim 1 wherein the unsaturated alpha-olefin is an unsaturated organic compound containing from 2 to 24 carbon atoms.

3. The process of claim 2 wherein the unsaturated alpha-olefin is a substituted or unsubstituted olefin, diolefin or cyclic olefin, wherein the substituent(s) is alkyl, phenyl, or alkylphenyl.

4. The process of claims 3 wherein the unsaturated alpha-olefin is 1-pentene, 1-octene, 1-dodecene, 1-tetradecene, 1-hexadecene, 1-eicosene, 2-hexene, 4-decene, 5-dodecene, 7-tetradecene, 9-eicosene or mixtures thereof.

5. The process of claim 4 wherein the alpha-olefin is 1-octene or 1-hexene.

6. The process of claim 1 wherein the oxidant is chlorine, hypochlorous acid or tert-butylhypochlorite.

7. The process of claim 6 wherein the oxidant is chlorine.

8. The process of claim 1 wherein the microemulsion of water and unsaturated alpha-olefin is prepared by adding a non-nucleophilic surfactant to the alpha-olefin or water and then blending the water and the olefin under conditions sufficient to form a microemulsion.

9. The process of claim 1 wherein the microemulsion of water and unsaturated alpha-olefin is prepared by blending the water and the olefin and then adding a non-nucleophilic surfactant to the blend under conditions sufficient to form a microemulsion.

10. The process of claim 8 wherein the non-nucleophilic surfactant is used with a co-surfactant.

11. The process of claim 8 wherein the non-nucleophilic surfactant is an alpha-olefin sulfonate, an alpha-olefin carboxylate or a quaternary amine.

12. The process of claim 11 wherein the quaternary amine is dodecyl trimethyl ammonium chloride, octadecyl trimethyl ammonium chloride, octadecyl pyridium chloride, didodecyl dimethyl ammonium chloride, tallow ammonium chloride or 1-benzyl-2-hexadecyl ammonium chloride.

13. The process of claim 10 wherein the co-surfactant is a non-nucleophilic alcohol, a non-nucleophilic carboxylate, or a non-nucleophilic hydrophilic organic acid.

14. The process of claim 13 wherein the organic acid is acetic acid, propionic acid or butyric acid.

15. The process of claim 13 wherein the alcohol is t-butanol, 1, 1-dimethyl-1-propanol or 1, 1-dimethyl-1butanol.

16. The process of claim 10 wherein the co-surfactant is the chlorohydrin formed during the reaction.

17. The process of claim 1 wherein the hypochlorination reaction is conducted at 0° C. to 120° C. and for a time sufficient for the reaction to occur.

18. The process of claim 17 wherein the hypochlorination reaction is conducted at about 20° C. to about 80° C. and for a time of from about 1 minute to about 2 hours, the time being residence time in a continuous reactor regime.

19. The process of claim 17 wherein the hypochlorination reaction is conducted for about 5 minutes to about 30 minutes or from about 10 minutes to about 15 minutes, the time being resonance time in a continuous reactor regime.

20. The process of claim 1 wherein the water and the alpha-olefin are employed in a water to alpha-olefin volume ratio of at least 5 to 1.

21. The process of claim 20 wherein the water to alpha-olefin volume ratio is at least 20 to 1.

22. The process of claim 20 wherein the water to alpha-olefins volume ratio does not exceed 100 to 1.

23. The process of claim 1 wherein the oxidant is employed in an amount of from about 0.8 to about 1.2 equivalents based on olefin.

24. The process of claim 1 wherein the oxidant is employed in an amount of from about 0.9 to about 1.1 equivalents based on olefin.

25. The process of claim 1 wherein the oxidant is employed in an amount of about 1.0 equivalent, based on olefin.

26. The process of claim 1 wherein the surfactant is employed in an amount of from about 0.01 to about 5 weight percent, based on the weight of olefin.

27. The process of claim 1 wherein the surfactant is employed in an amount of from about 0.1 to about 2 weight percent, based on the weight of olefin.

28. The process of claim 1 wherein the surfactant is employed in an amount of from about 2 to about 1.5 weight percent, based on the weight of olefin.

29. The process of claim 1 wherein the surfactant is employed in an amount of from about 0.3 to 1.0 weight percent, based on the weight of olefin.

* * * * *